(12) United States Patent
Duma

(10) Patent No.: US 11,730,767 B2
(45) Date of Patent: Aug. 22, 2023

(54) METHODS, APPARATUSES AND SYSTEMS FOR INSTILLING STEM CELLS AND PHARMACEUTICALS INTO THE HUMAN VENTRICULAR SYSTEM

(71) Applicant: Regeneration Biomedical, Inc., Newport Beach, CA (US)

(72) Inventor: Christopher Duma, Newport Beach, CA (US)

(73) Assignee: Regeneration Biomedical, Inc., Newport Beach, CA (US)

( * ) Notice: Subject to any disclaimer, the term of this patent is extended or adjusted under 35 U.S.C. 154(b) by 1188 days.

(21) Appl. No.: 16/283,466

(22) Filed: Feb. 22, 2019

(65) Prior Publication Data

US 2019/0262403 A1 Aug. 29, 2019

Related U.S. Application Data

(60) Provisional application No. 62/634,773, filed on Feb. 23, 2018.

(51) Int. Cl.
*A61K 35/28* (2015.01)
*A61P 25/28* (2006.01)
(Continued)

(52) U.S. Cl.
CPC ............ *A61K 35/28* (2013.01); *A61K 9/0085* (2013.01); *A61M 27/006* (2013.01); *A61P 25/28* (2018.01);
(Continued)

(58) Field of Classification Search
CPC ... A61K 35/28; A61K 9/0085; A61M 27/006; A61M 5/178; A61M 39/0208;
(Continued)

(56) References Cited

U.S. PATENT DOCUMENTS 5,222,982 A 6/1993 Ommaya
5,385,582 A 1/1995 Ommaya
(Continued)

FOREIGN PATENT DOCUMENTS

WO 2016009446 A2 1/2016

OTHER PUBLICATIONS

Frequently Asked Questions about Ommaya Reservoirs and Ommaya Taps. Memorial Sloan Kettering Cancer Center, 2017 [retrievedApr. 29, 2019] Retrieved from the internet <http://www.mskcc.org/cancer-care/patient-education/frequently-asked-questions-about-ommaya-reservoirs-and-ommaya-taps>, entiredocument.*
(Continued)

*Primary Examiner* — Theodore J Stigell
(74) *Attorney, Agent, or Firm* — Irell and Manella LLP

(57) ABSTRACT

The METHODS, APPARATUSES AND SYSTEMS FOR INSTILLING STEM CELLS AND PHARMACEUTICALS INTO THE HUMAN VENTRICULAR SYSTEM (hereinafter "Ventricular Stem Cell System" or "VSCS") disclosed herein provide safe and effective techniques for obtaining stem cells and instilling any type of stem cell or pharmaceutical agents into the human ventricular system for treatment of various diseases, including neurodegenerative diseases such as Parkinson's, Alzheimer's, Multiple Sclerosis, and others.

18 Claims, 16 Drawing Sheets

(51) Int. Cl.
| | |
|---|---|
| A61M 27/00 | (2006.01) |
| A61K 9/00 | (2006.01) |
| A61M 39/02 | (2006.01) |
| A61M 5/178 | (2006.01) |

(52) U.S. Cl.
CPC ......... *A61M 5/178* (2013.01); *A61M 39/0208* (2013.01); *A61M 2039/025* (2013.01); *A61M 2202/0437* (2013.01); *A61M 2202/08* (2013.01)

(58) Field of Classification Search
CPC .... A61M 2039/025; A61M 2202/0437; A61M 2202/08; A61P 25/28
See application file for complete search history.

(56) References Cited

U.S. PATENT DOCUMENTS

| | | | |
|---|---|---|---|
| 5,720,720 A | 2/1998 | Laske et al. | |
| 5,753,505 A | 5/1998 | Luskin | |
| 7,442,372 B2 | 10/2008 | Kakkis | |
| 7,582,292 B2* | 9/2009 | Wilkison | A61P 25/00 435/368 |
| 7,670,838 B2 | 3/2010 | Deisseroth et al. | |
| 8,282,593 B2 | 10/2012 | Dacey, Jr. et al. | |
| 2003/0092176 A1* | 5/2003 | Janson | A61P 27/16 435/368 |
| 2010/0119496 A1* | 5/2010 | Wilkison | A61P 25/00 435/366 |
| 2010/0286585 A1 | 11/2010 | DiMauro et al. | |
| 2014/0127171 A1* | 5/2014 | Nocera | A61K 49/0004 514/355 |
| 2019/0224245 A1* | 7/2019 | Katz | B01L 3/5021 |
| 2022/0288128 A1* | 9/2022 | Kumar | A61K 35/28 |

OTHER PUBLICATIONS

Volkov, et al., Surgical Treatment for Leptomeningeal Disease., 2017 [retrieved Apr. 29, 2019],Retrieved from the internet,entire document.*

Standardized Procedure Intraventricular Chemotherapy Via Ommaya Reservoir (Adult, Peds).University of California San Diego (UCSD),2016, [retrieved Apr. 29, 2019],Retrieved from the internet <http://health.ucsd.edu/medinfo/medical-staff/application/Documents/SP6%20Intraventricular%20Chemo%20Via%20Ommaya%20Reservoir%20(Adult-Peds).pdf>,entiredocument.*

International Search Report and the Written Opinion of the International Search Authority; PCT/US19/19294 dated May 15, 2019; entire document.

Frequently Asked Questions about Ommaya Reservoirs and Ommaya Taps. Memorial Sloan Kettering Cancer Center, 2017 [retrieved Apr. 29, 2019] Retrieved from the internet <https://www.mskcc.org/cancer-care/patient-education/frequently-asked-questions-about-ommaya-reservoirs-and-ommaya-taps>, entire document.

Volkov, et al., Surgical Treatment for Leptomeningeal Disease., 2017 [retrieved Apr. 29, 2019], Retrieved from the Internet< https://moffitt.org/media/6008/47.pdf>, entire document.

Standardized Procedure Intraventricular Chemotherapy Via Ommaya Reservoir (Adult, Peds). University of California San Diego (UCSD), 2016 [retrieved Apr. 29, 2019], Retrieved from the internet <https://health.ucsdedu/medinfo/medical-staff/application/Documents/SP6%20Intraventricular%20Chemo%20Via%20Ommaya%20Reservoir%20(Adult-Peds).pdf>, entire document.

L. Casteilla et al., Adipose-derived stromal cells: Their identity and uses in clinical trials, an update, World J. Stem Cells, 3(4): 25-33 (Apr. 26, 2011) (https://www.ncbi.nlm.nih.gov/pmc/articles/PMC3097937/).

Salehi, Hossein et al., "An Overview of Neutral Differentiation Potential of Human Adipose Derived Stem Cells", Stem Cell Rev and Rep (2016), 12:26-41, Published Online Oct. 21, 2015, Springer Science+Business Media, New York, 2015.

Chakar, Diana, "Hepatic potential of Reversed-age Mesenchymal Stem Cells and Endodermal Progenitors: Contribution of LGR5 and Cdc42 cell signaling pathways", Ph.D. dissertation, HAL archives-ouvertes, submitted Aug. 31, 2018, pp. 1-215, Universite Paris-Saclay, Universite libanaise, http://tel.archives-ouvertes.fr/tel-01865143.

Supplementary European Search Report, EP Application No. 19863703.5, dated May 11, 2022.

* cited by examiner

_US 11,730,767 B2_

METHODS, APPARATUSES AND SYSTEMS FOR INSTILLING STEM CELLS AND PHARMACEUTICALS INTO THE HUMAN VENTRICULAR SYSTEM

PRIORITY CLAIM AND RELATED APPLICATIONS

This application is a non-provisional of and claims priority under 35 U.S.C. § 119(e) to prior U.S. provisional application for patent Ser. No. 62/634,773, filed Feb. 23, 2018, entitled, "METHODS AND APPARATUSES FOR INSTILLING STEM CELLS AND PHARMACEUTICALS INTO THE HUMAN VENTRICULAR SYSTEM,". The entire contents of the aforementioned application are hereby expressly incorporated herein by reference.

This application for letters patent disclosure document describes inventive aspects that include various novel innovations (hereinafter "disclosure") and contains material that is subject to copyright, and/or other intellectual property protection. The respective owners of such intellectual property have no objection to the facsimile reproduction of the disclosure by anyone as it appears in published Patent Office file/records, but otherwise reserve all rights.

FIELD

The present innovations generally address treatment of diseases such as neurodegenerative diseases, and more particularly, include METHODS, APPARATUSES AND SYSTEMS FOR INSTILLING STEM CELLS AND PHARMACEUTICALS INTO THE HUMAN VENTRICULAR SYSTEM.

BACKGROUND

Neurological damage and neurodegenerative diseases were long thought to be irreversible because of the inability of neurons and other cells of the nervous system to grow in the adult body. However, the recent advent of stem cell-based therapy for tissue repair and regeneration provides promising treatments for a number of neurodegenerated pathologies and other neurological disorders. Stem cells are capable of self-renewal and differentiation to generate a variety of mature neural cell lineages. Pharmaceuticals may also be used such as trophic factors, immunoglobulins and others to treat neurological disorders.

Delivery of stem cells into the human ventricular system using an Ommaya Reservoir has been reported, including: (1) Fauzi A A, Suroto N S, Bajamal A H, Machfoed M N, Intraventricular Transplantation of Autologous Bone Marrow Mesenchymal Stem Cells via Ommaya Reservoir in Persistent Vegetative State Patients after Haemorrhagic Stroke: Report of Two Cases & Review of the Literature, J Stem Cells Regen Med 2016; 12(2):100-104; and (2) Back W, Kim Y S, Koh S H, Lim S W, Kim H Y, Yi H J, Kim H., Stem cell transplantation into the intraventricular space via an Ommaya reservoir in a patient with amyotrophic lateral sclerosis, J Neurosurg Sci 2012; 56(3):261-3. The authors of these publications used autologous mesenchymal stem cells derived from bone marrow.

SUMMARY

The METHODS, APPARATUSES AND SYSTEMS FOR INSTILLING STEM CELLS AND PHARMACEUTICALS INTO THE HUMAN VENTRICULAR SYSTEM (hereinafter "Ventricular Stem Cell System" or "VSCS") disclosed herein in various embodiments provide safe and effective techniques for obtaining stem cells and instilling any type of stem cell or pharmaceutical agents into the human ventricular system for treatment of various diseases, including neurodegenerative diseases such as Parkinson's, Alzheimer's; Multiple Sclerosis, and others.

In one embodiment, a method is disclosed, comprising: inserting a needle attached to a first syringe into an injection site for at least one reservoir coupled to a ventricular system of a brain; withdrawing a first volume of cerebrospinal fluid using the first syringe; exchanging the first syringe attached to the needle with a second syringe, the second syringe containing a therapeutic suspension; injecting the therapeutic suspension into the reservoir; flushing the reservoir with a portion of the first volume of cerebrospinal fluid; and removing the needle and dressing the injection site.

In another embodiment, a system is disclosed, comprising: at least one implanted reservoir coupled to a ventricular system of a brain; and at least one injector configured to deliver a therapeutic suspension comprising a stromal vascular fraction to the ventricular system of the brain via the at least one implanted reservoir.

BRIEF DESCRIPTION OF THE DRAWINGS

The accompanying appendices and/or drawings illustrate various non-limiting, exemplary, innovative aspects in accordance with the present descriptions.

DETAILED DESCRIPTION

Figure 1:
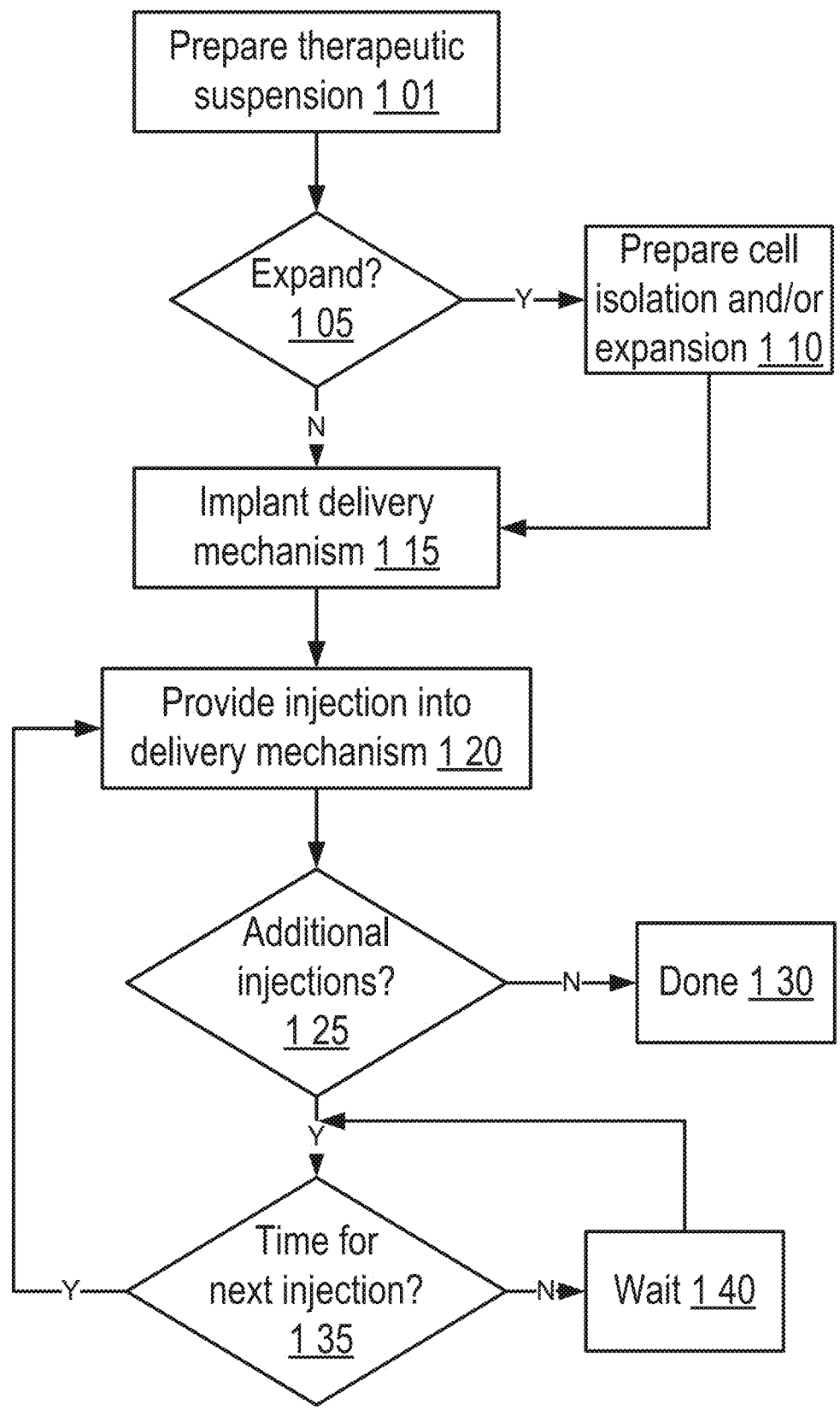
FIG. 1 shows an example of logic flow for delivery of therapeutic suspensions in accordance with the VSCS in one embodiment.

The METHODS, APPARATUSES AND SYSTEMS FOR INSTILLING STEM CELLS AND PHARMACEUTICALS INTO THE HUMAN VENTRICULAR SYSTEM (hereinafter "Ventricular Stem Cell System" or "VSCS") disclosed herein in various embodiments provide safe and effective techniques for obtaining stem cells and instilling any type of stem cell and/or pharmaceutical agents (e.g., those used for the treatment of neurodegenerative diseases, and/or those used to supplement stem cell injections) into the human ventricular system for treatment of various diseases, including neurodegenerative diseases such as Parkinson's Disease, Alzheimer's Disease, Amyotrophic Lateral Sclerosis Multiple Sclerosis, and others. Although the abbreviated title, "Ventricular Stem Cell System" or "VSCS," refers to stem cells, it should be understood that the disclosed apparatuses, methods and systems include delivery of pharmaceuticals and/or other therapeutic suspensions in addition to and/or instead of stem cells.

Certain stem cells comprise neural stem cells, haematopoietic stem cells, and mesenchymal stem cells, and may be autologous or allogeneic in various embodiments. In recent years, mesenchymal stem cells have been used to treat certain human neurodegenerative disorders. Mesenchymal stem cells can be found in various adult tissues and, compared to stem cells from the embryo or fetus, adult mesenchymal stem cells lack cultural controversy. However, difficulties associated with obtaining therapeutic quantities of stem cells and administrating a safe and effective route and site for stem cell delivery remain significant issues. Similarly, diseases including multiple sclerosis and Amyotrophic Lateral Sclerosis (ALS) may have an inflammatory component amenable to intraventricular injection of an anti-inflammatory pharmaceutical.

Delivery methods that have been used in some cases to deliver stem cells include: intraparenchymal and systemic. Intraparenchymal or intracerebral injection (injection directly into the substance of the brain) presents a significant degree of two major common neurosurgical risks bleeding and infection. Furthermore, even though there are reports of a high level of migratory capability of stem cells in animal experiments, it is difficult to expect the stem cells to repopulate the entire human brain and/or spinal cord, which can be important for efficacy of the treatment of the disorders with widely spread neuronal degeneration. Another disadvantage of the intraparenchymal injection is unavoidable, albeit transient, disruption of the Blood Brain Barrier. Another limitation for using direct intraparenchymal injection is that such an approach does not allow for injection of large numbers of the stem cells due to comparatively high density of the brain tissue. Intravenous and intra-arterial delivery routes have also experienced less than ideal outcomes. Intravenous injections have been employed for the treatment of orthopedic, cardiovascular, and erectile disorders. But up to 90% of the cells injected intravenously may be trapped in the lungs compared to intra-arterial injections. Because many of the stem cells do not reach the brain tissue due to entrapment of the majority of the stem cells in the lungs, this method is not ideal for treating neurodegenerative disorders. Intra-arterial delivery provides a better biodistribution of the stem cells through the brain but increases the risk of cerebral lesions/microstrokes. Some treatments have employed autologous mesenchymal stem cells derived from bone marrow. Bone marrow harvest is universally painful to the donor, and mesenchymal stem cells are normally present at very low frequencies in bone marrow.

In embodiments of the disclosed VSCS, stem cells or pharmaceuticals may be injected into the ventricles of the brain for treatment of various diseases via an implanted Ommaya reservoir, ventriculoperitoneal shunt, catheter, tube, cannula, and/or the like. Because the ventricular system responsible for irrigating all of the brain parenchyma, including the brain's lymphatic system, this route of injection is effective for delivering the treatment throughout the brain. For example, embryonal, fetal, adult, mesenchymal, neuronal, adipose, and bone marrow stem cells as well as any other types of stem cells or immunoglobulin, trophic factors or any other chemical or pharmaceutical beneficial to treatment of neurodegenerative diseases can be injected to treat diseases including Parkinson's, Alzheimer's, Multiple Sclerosis, and others, in accordance with embodiments of the invention.

FIG. 1 shows an example of logic flow for delivery of therapeutic suspensions in accordance with the VSCS in one embodiment. A therapeutic suspension, such as a stem cell and/or pharmaceutical suspension, is prepared 101. In the case of a stem cell suspension, a determination may be made as to whether to expand the stem cells 105 and, if desired, such expansion may be effected, such as via cell isolation and expansion in a certified cell bank 110. A delivery mechanism may then be implanted, such as an Ommaya reservoir, ventriculoperitoneal shunt, catheter, tube, cannula, and/or the like 115. Injections of the therapeutic suspension may then be provided to the ventricular regions of the brain via the delivery mechanism 120. Determination may be made as to whether additional injections are warranted or desired 125. If not, the process concludes 130. Otherwise, a determination may be made as to whether adequate time has passed for the injection to be made 135, such as based on scheduling, doctor recommendation, transpiring of a predetermined injection period, and/or the like. If sufficient time has not passed, a wait period may be entered 140. Otherwise, the process may return to 120 and provide one or more additional injections.

In one embodiment of the invention, the stem cells injected into the ventricles of the brain are adipose derived mesenchymal stem cells. Although adipose derived mesenchymal stem cells, stromal vascular fraction, and/or the like are described in various examples herein, it should be understood that other stem cells and/or methods of stem cell preparation may also be employed in conjunction with embodiments of the VSCS. Adipose derived mesenchymal stem cells can differentiate into many different kinds of specialized cells, for example muscle, cardiac, nerve, bone, cartilage, fat, liver, and/or the like cells. Adipose derived mesenchymal stem cells also carry advantages over other types of stem cells such as bone marrow mesenchymal stem cells. For example, the extraction process for adipose stem cells derived from abdominal fat is easier and less painful, and the stem cells can be obtained in large quantities with significantly less invasive and safer methods. Moreover, they can differentiate toward neurogenic lineage, and transplantation of adipose derived stem cells also may promote the peripheral nerve regeneration including in part through paracrine secretion of trophic factors.

Figure 2:
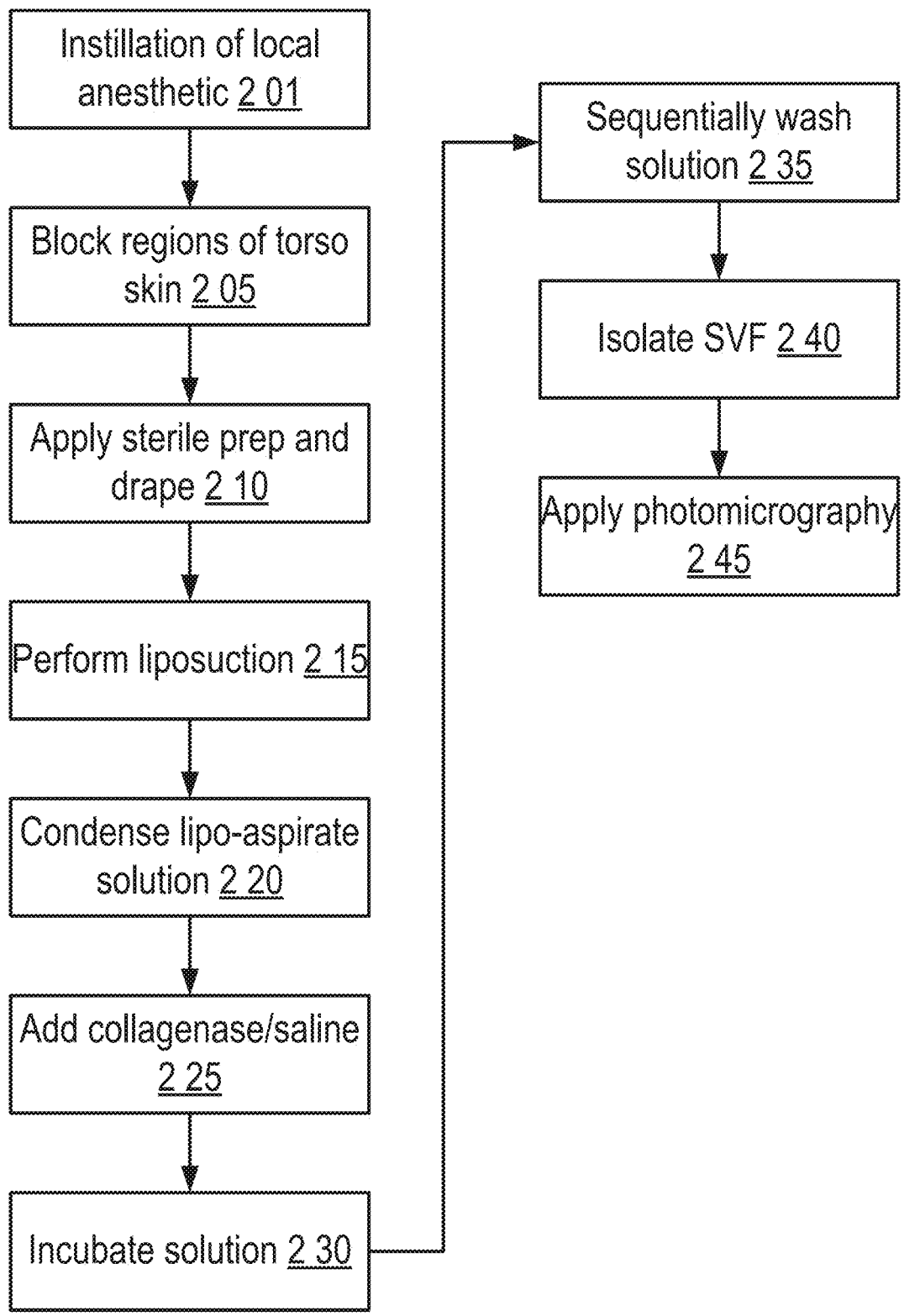
FIG. 2 shows an example of logic flow for isolation of the Stromal Vascular Fraction containing adipose derived stem cells in one embodiment.
Figure 3:
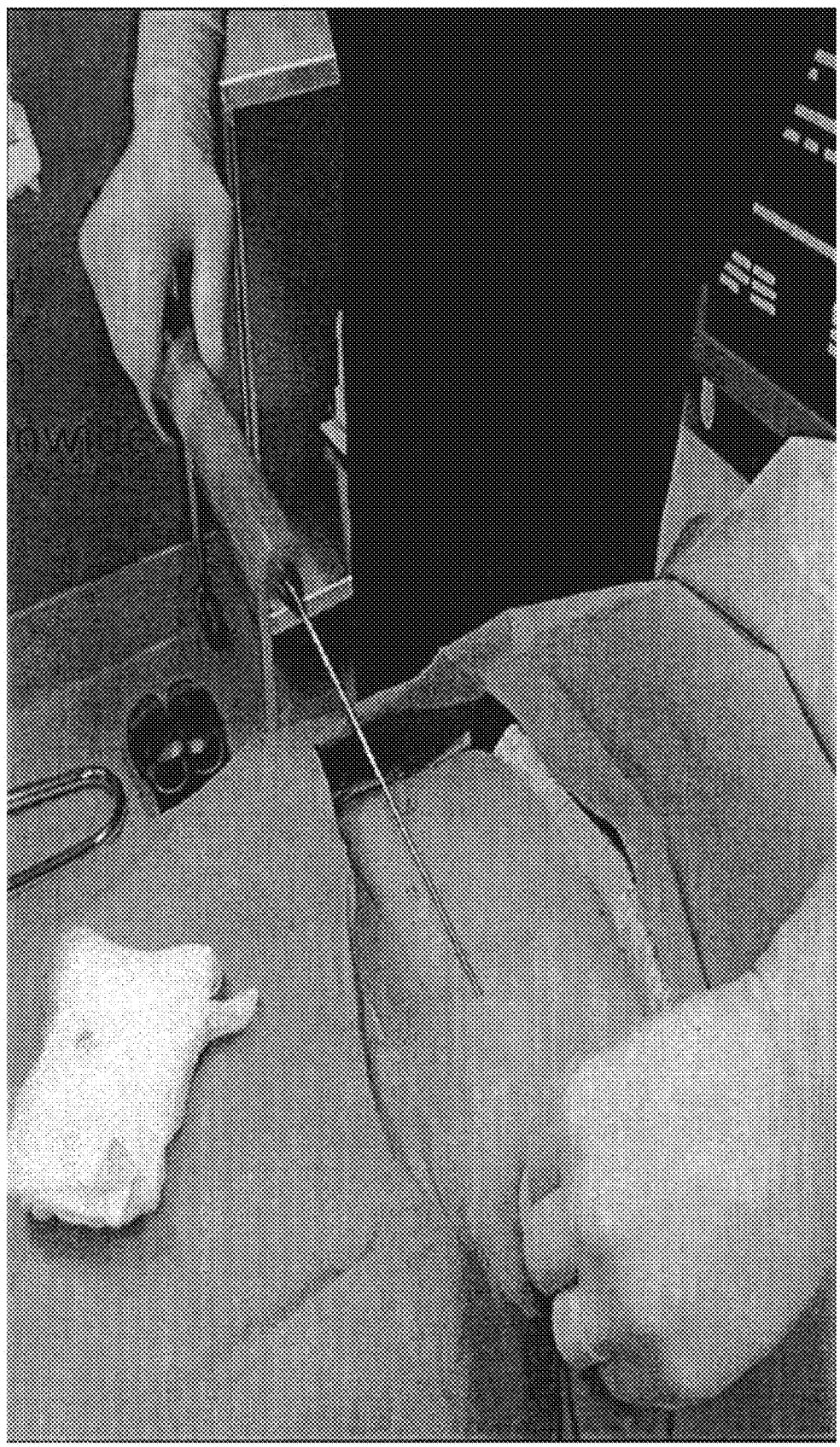
FIG. 3 shows an example of a liposuction procedure that may be used to harvest cells in one embodiment of a VSCS.
Figure 4:
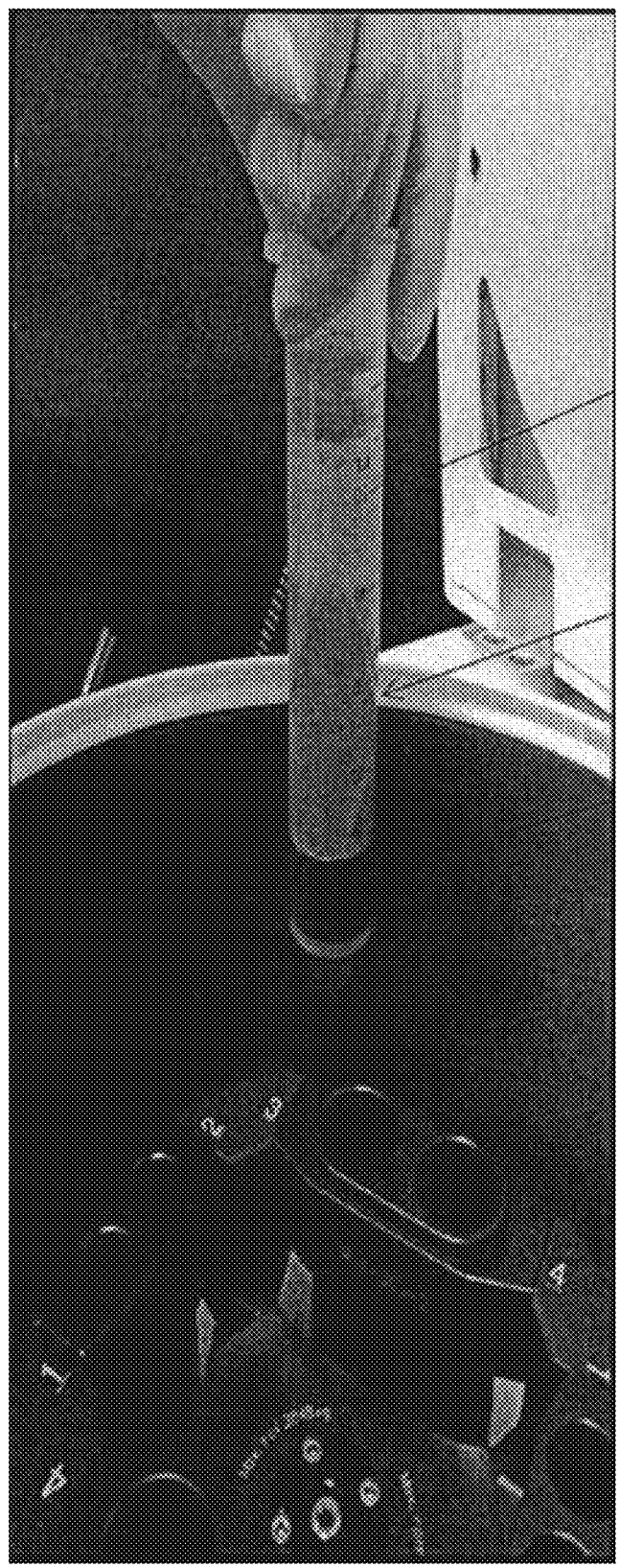
FIG. 4 shows an example of centrifugation of harvested cells in one embodiment of a VSCS.
Figure 5:
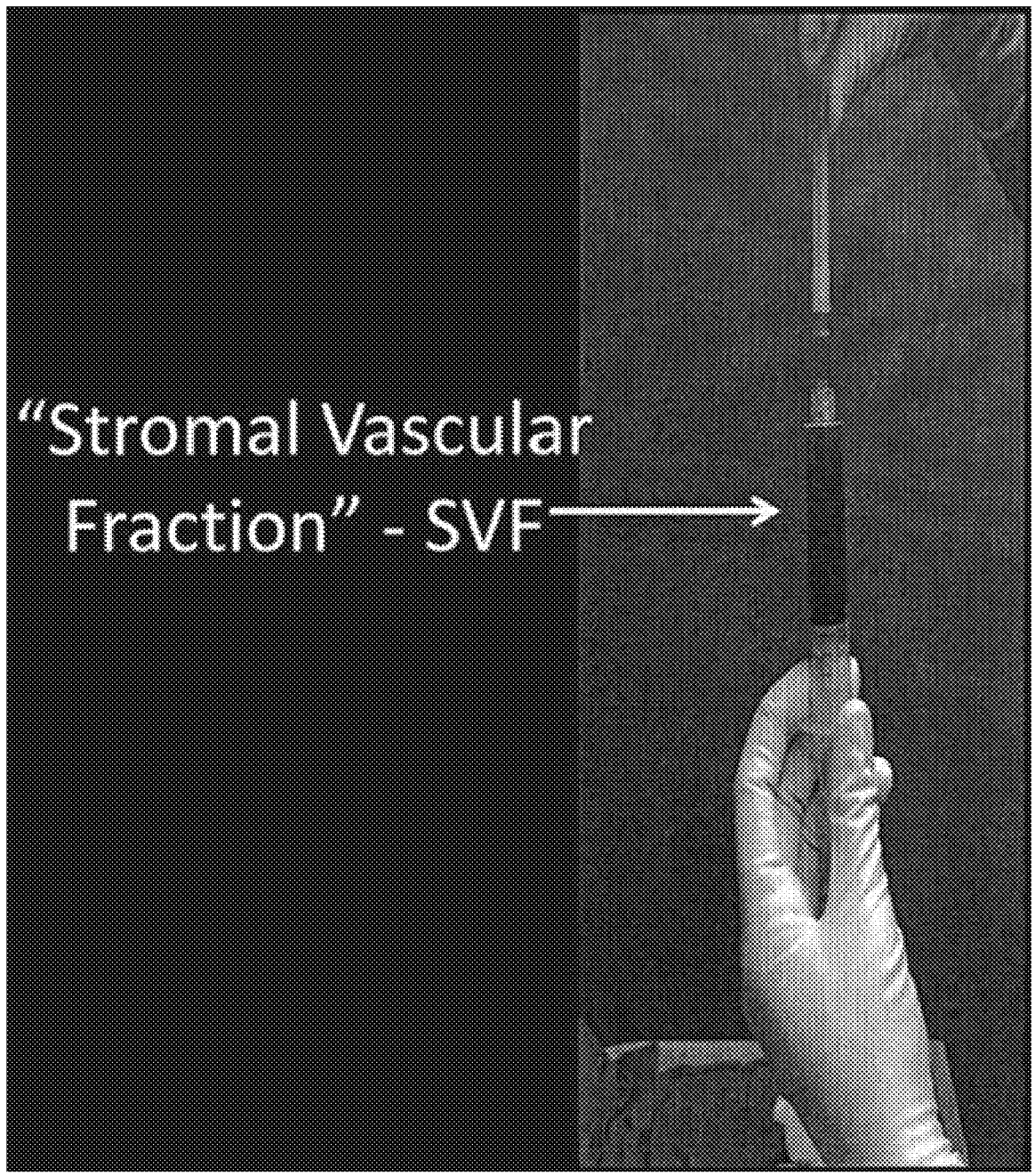
FIG. 5 shows incubated and isolated SVF cells or, ultimately, stem cells in one embodiment of a VSCS.
Figure 6:
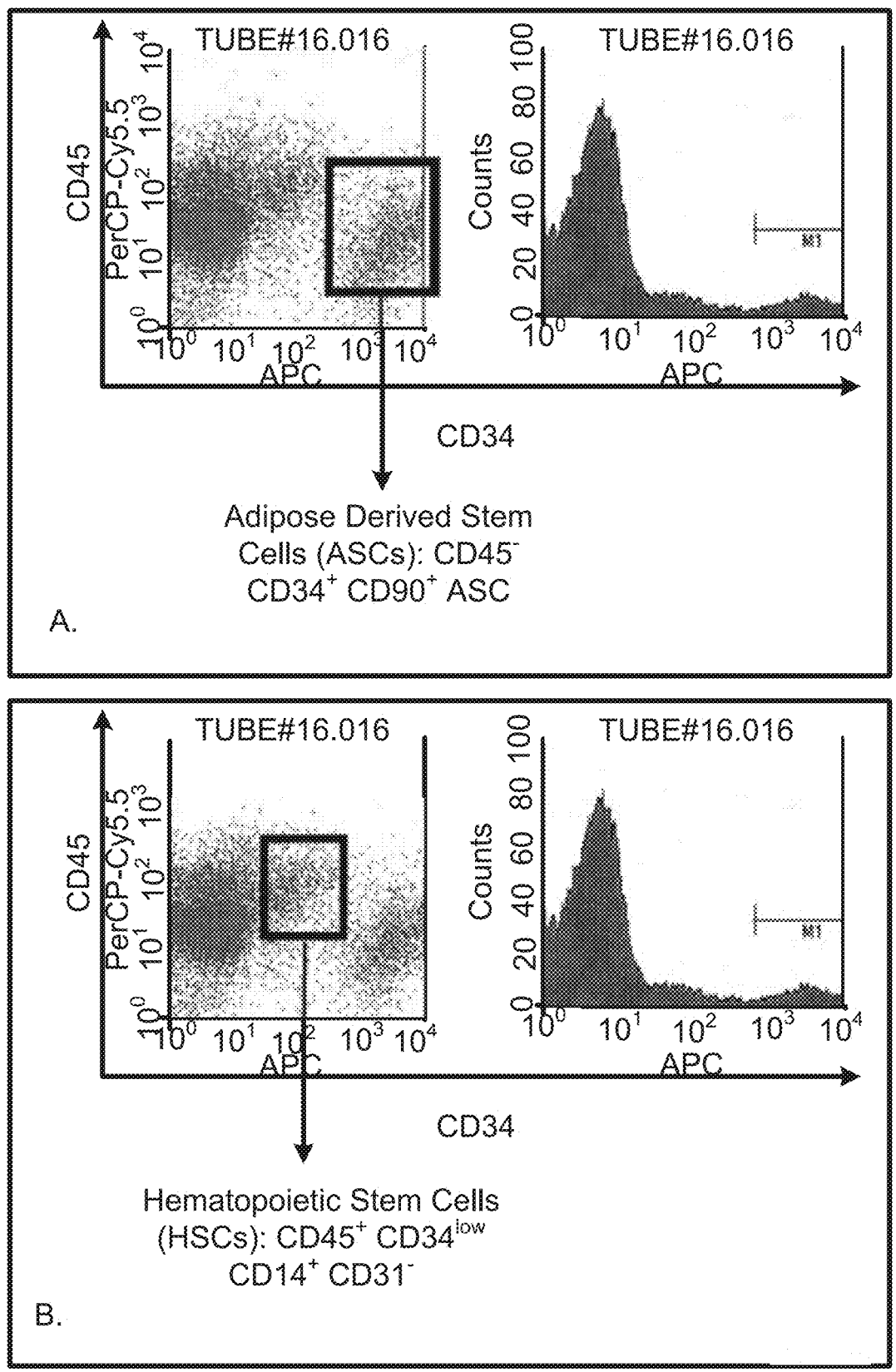
FIG. 6 shows an example of flow cytometry of Stromal Vascular Fraction samples distinguishing adipose derived stem cells (A) from hematopoietic stem cells (B), in one embodiment of a VSCS.

In one embodiment, the adipose derived mesenchymal stem cells are prepared from adipose tissue obtained by liposuction, from direct surgical excision, and/or the like, which may be minimally invasive procedures. The adipose tissue may be obtained from a human, e.g., from the patient who is the intended recipient of the therapeutic stem cells. FIG. 2 shows an example of logic flow for isolation of the Stromal Vascular Fraction (or "SVF") containing adipose derived stem cells in one embodiment. For example, patients may undergo instillation of local anesthetic 201 consisting of lidocaine 0.5% with epinephrine 1:400,000 and sodium bicarbonate 8.4%. Using a sub-dermal non-tumescent method, small regions of torso skin (approximately 20 cm2) may be blocked (e.g., abdominal or posterior flanks) 205. The patient may then receive sterile prep and drape 210. A specialized surgical processing system (e.g., the CSN Time Machine® system, trademark name for the MediKhan Lipokit/Maxstem system; MediKhan, Los Angeles, Calif.; 510 K approved for fat grafting) can be used to harvest, centrifuge, incubate, and isolate the Stromal Vascular Fraction cells. Within 2 minutes of local anesthetic injection, a mini liposuction may be performed 215, e.g., through a number 11-blade puncture wound using the negative pressure syringe technique with a TP101 syringe and a 3-mm cannula. An amount, e.g., approximately 50 cubic centimeters, of the lipo-aspirate solution can be obtained and condensed by centrifugation 220, at 2800 rpm for 3 minutes in the Time Machine® centrifuge, 12.5 Wunsch units of T-MAX® Good Manufacturing Practices (GMP) grade bacteria-produced collagenase (private label name for Liberase by Roche, Ind.) in 25 cc of normal saline may be added 225, in one implementation, to 25 cc of condensed fat and incubated at 38° C. in the Time Machine® incubator for 30 minutes to digest the collagen matrix to procure the Stromal Vascular Fraction in closed Time Machine Syringes (TP-102 syringe by MediKhan). In one implementation, the product can be washed with DSLR sequentially 235 (e.g., 3 times) and then the Stromal Vascular Fraction concentrate can be isolated 240. In one implementation, Stromal Vascular Fraction can be filtered through a Food and Drug Administration (FDA)-approved 100-μm nylon filter, cell strainer, and/or the like (e.g., 131) Falcon cell strainer; Becton Dickinson, Franklin Lakes, N.J.). Photomicrography, e.g., using the Invitrogen by Countess (Invitrogen, ThermoFisher Scientific, Waltham, Mass.) can be used to document lack of aggregation, allow for a basic cell count, and measure cell viability using 0.4% trypan blue 245. FIG. 3 shows an example of a liposuction procedure that may be used to harvest cells in one embodiment of a VSCS. FIG. 4 shows an example of centrifugation of harvested cells in one embodiment of a VSCS. FIG. 5 shows incubated and isolated SVF cells or, ultimately, stem cells in one embodiment of a VSCS. FIG. 6 shows an example of flow cytometry of Stromal Vascular Fraction samples distinguishing adipose derived stem cells (A) from hematopoietic stem cells (B), in one embodiment of a VSCS.

In further embodiments, the stem cells, such as the adipose derived cells, may be expanded using an exemplary procedure such as cell isolation and expansion in a certified cell bank.

In embodiments of the VSCS, stem cells and expanded stem cells can be delivered via an implanted Ommaya reservoir, ventriculoperitoneal shunt, catheter, tube, cannula, and/or the like. For example, the Stromal Vascular Fraction containing adipose derived stem cells, the expanded purified form of stem cell, and/or a pharmaceutical can be injected into the brain via an Ommaya reservoir or ventriculoperitoneal shunt that is implanted into the brain.

Figure 7:
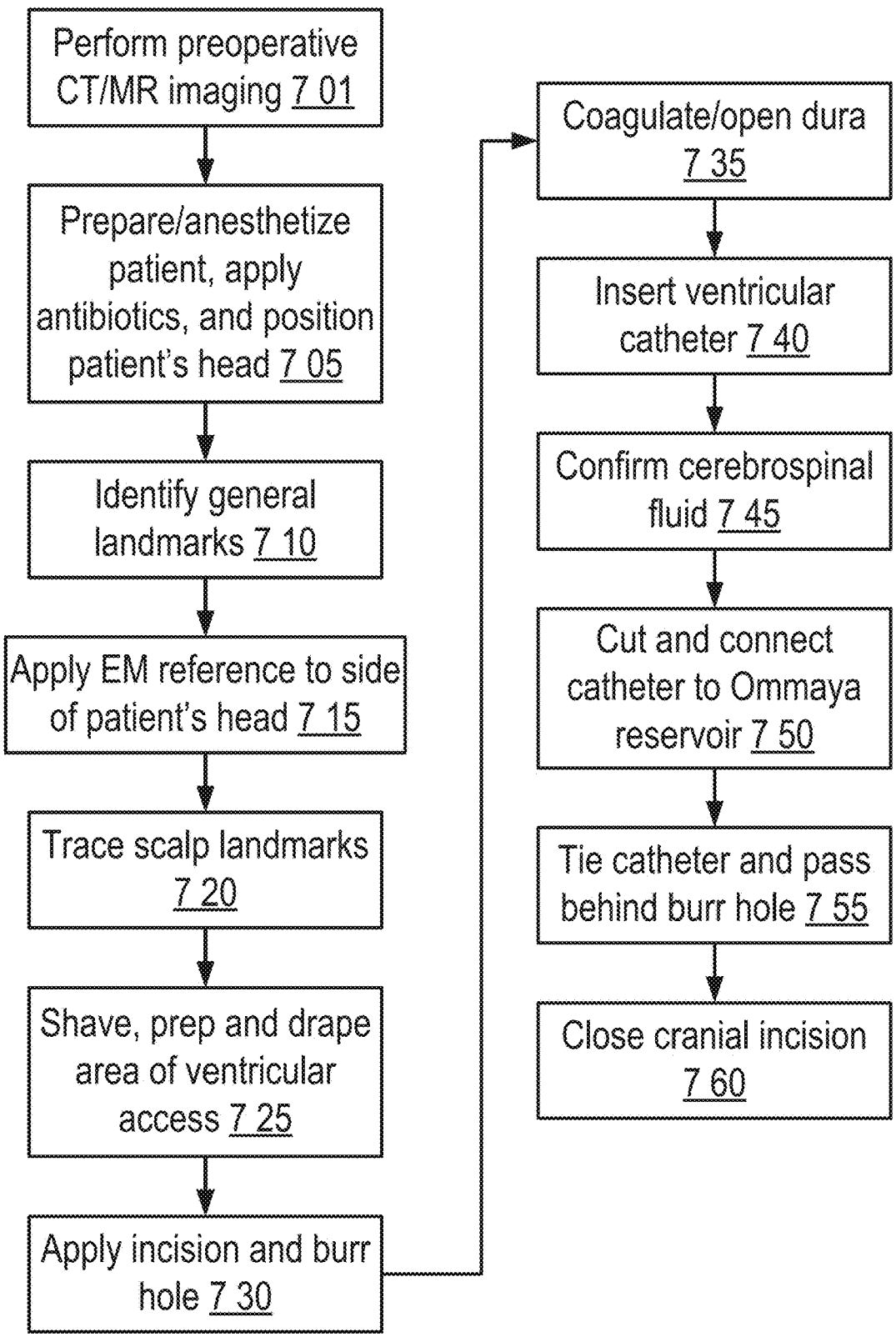
FIG. 7 shows an example of logic flow for implantation of an Ommaya reservoir in one embodiment of a VSCS.
Figure 8:
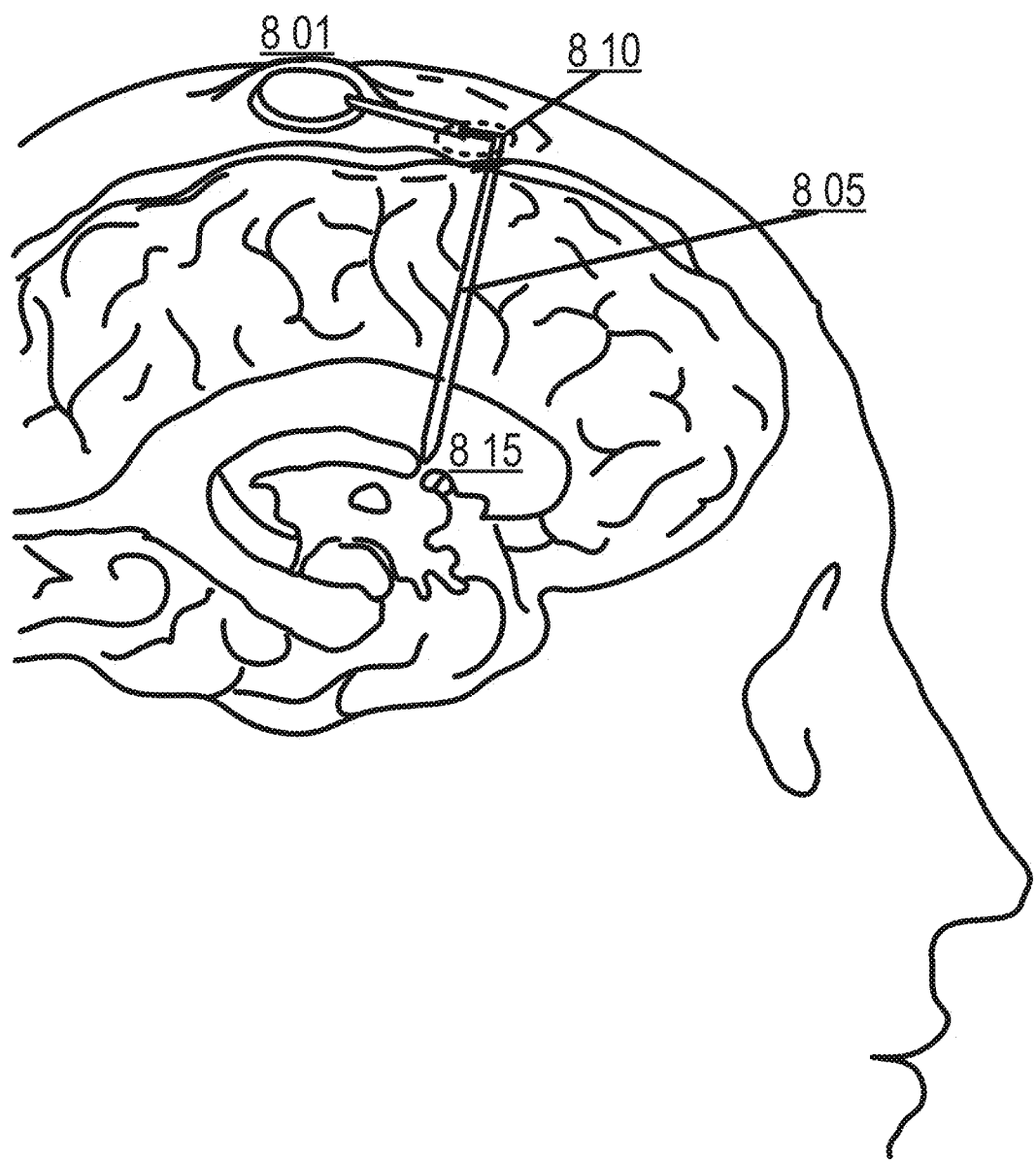
FIG. 8 shows an example of subgaleal placement of Ommaya reservoir (or alternatively with a ventriculoperitoneal shunt) with right-angle connection of right frontal intraventricular catheter in one embodiment of a VSCS.

In one embodiment, a reservoir, such as an Ommaya reservoir, is implanted in the brain for instilling any type of stem cell or pharmaceutical into the human ventricular system for treatment of various diseases, including neurodegenerative diseases such as Parkinson's, Alzheimer's, Multiple Sclerosis, and others. In one implementation, the reservoir can be implanted using the following procedure. FIG. 7 shows an example of logic flow for implantation of an Ommaya reservoir in one embodiment of a VSCS. For example, implantation of the reservoir may begin with preoperative CT or MR imaging on the patient 701. After the patient is prepared, a suitable plane of general endotracheal anesthesia may be achieved, antibiotics may be administered, and the patient's head may be placed on a donut 705. General landmarks may be identified 710 and a device such as the Stealth-Axiem© system (Medtronic, Inc.) can receive the downloaded MRI images. The electromagnetic reference can be applied to the side of the patient's head and secured 715. The patient's scalp landmarks can be traced 720 obtaining an accuracy better than, e.g., 2 mm for computer navigation. The area of the right frontal region or any site of ventricular access, can be shaved, prepped and draped 725. The planned incision, e.g., 3 cm lateral to midline and 2 cm anterior to the coronal suture, can be infiltrated with 1:200,000 epinephrine solution of 1% lidocaine. The incision can be made, for example, using a 10-blade scalpel. A burr-hole or the like can be made at the frontal incision, such as by using an acorn drill bit 730. The dura may be coagulated with a bipolar cautery and opened 735, for example, using an 11-blade scalpel. The leaves of dura may be coagulated to the edges of the burr-hole and bleeding may be managed, such as with bipolar electrocautery. The ventricular catheter may be passed to, e.g., a 4-6 cm depth using a computer guidance system 740. Cerebrospinal Fluid flow from the catheter may be confirmed 745. The catheter may then be cut and connected with the Ommaya reservoir 750. The catheter can then be tied, e.g., using a 2-0 silk tie and passed subgalealy behind the burr-hole 755. The cranial incision may be closed, e.g., using 2-0 Vicryl sutures on the galeal, and staples on the skin 760. FIG. 8 shows an example of subgaleal placement of Ommaya reservoir (or alternatively with a ventriculoperitoneal shunt) with right-angle connection of right frontal intraventricular catheter in one embodiment of a VSCS. The Ommaya reservoir is shown at 801 with catheter 805 extending through burr hole 810 into the ventricular region 815 of the patient's brain.

Figure 9:
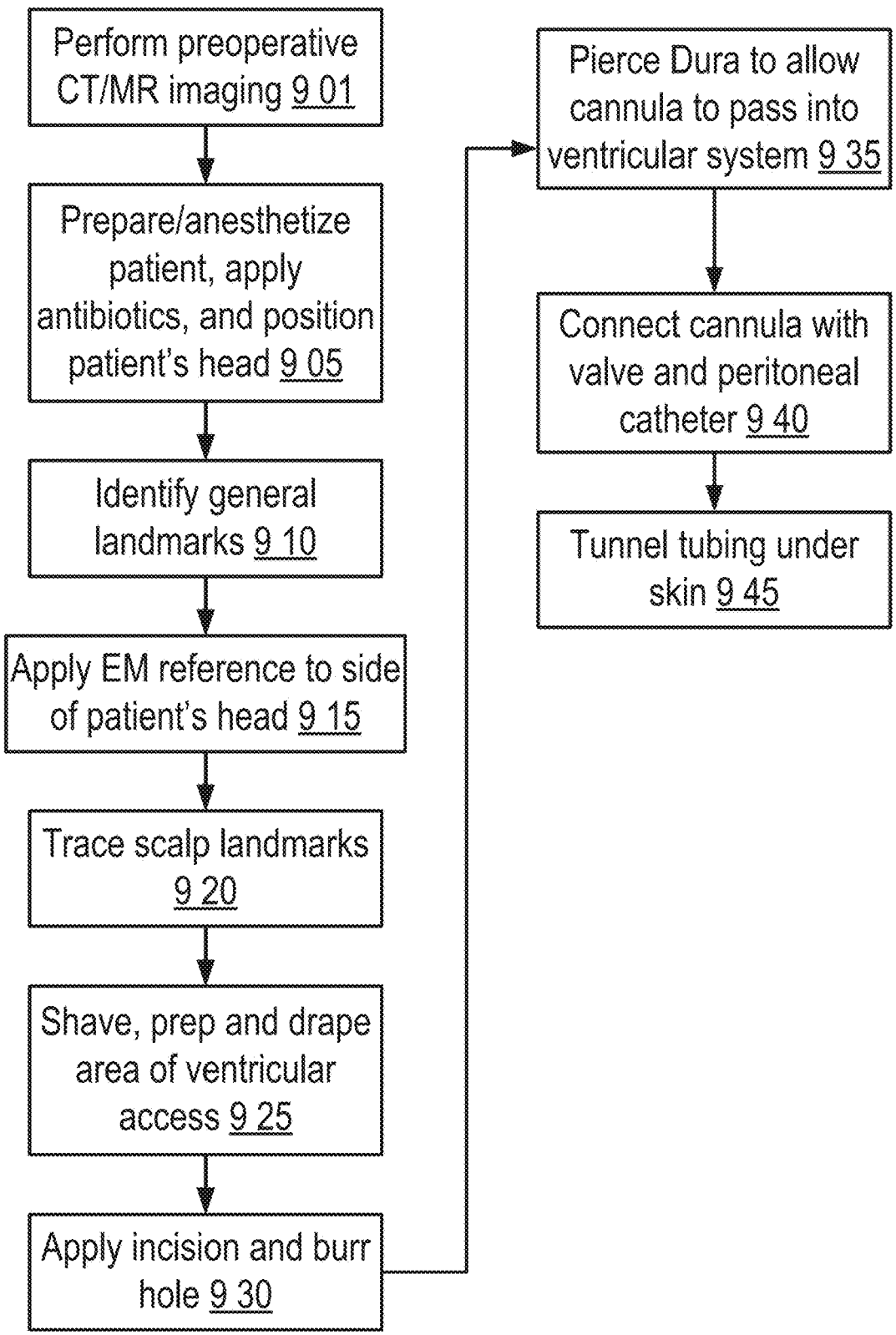
FIG. 9 shows an example of logic flow for implantation of a ventriculoperitoneal shunt in one embodiment of a VSCS.

In another embodiment, a ventriculoperitoneal shunt, rather than an Ommaya reservoir, is implanted for instilling any type of stem cell or pharmaceutical into the human ventricular system for treatment of various diseases, including neurodegenerative diseases such as Parkinson's, Alzheimer's, Multiple Sclerosis, and others. FIG. 9 shows an example of logic flow for implantation of a ventriculoperitoneal shunt in one embodiment of a VSCS. A preoperative CT and/or MR imaging may be performed 901 and the patient may be prepped and anesthetized, antibiotics applied, and the patient's head appropriately positioned 905. General landmarks may be identified 910, an EM reference may be applied to the side of the patient's head 915, and scalp landmarks may be traced 920. The area of ventricular access may then be shaved, prepared and draped 925. A 1-inch incision is made in this scalp at a predetermined area (e.g., frontal or occipital entry site). A burr-hole may be created, e.g., using a drill bit 930 and the dura is pierced to allow a cannula to be passed into the ventricular system 935. In one implementation, this may be performed using three-dimensional computer guidance. Once flow of cerebrospinal fluid is confirmed this cannula is connected in series with a valve 940, which may be programmable in one embodiment, and a peritoneal catheter which is implanted into the abdominal cavity through a separate incision. The tubing is tunneled under the skin using a separate technique 945, e.g., by using a subcutaneous tunneler through which a catheter is fed and ultimately implanted into the abdominal cavity, such as through laparoscopic or open surgical technique.

A ventriculoperitoneal shunt provides several advantages over an Ommaya reservoir. For example, one possible risk of the procedure utilizing the Ommaya reservoir is obstruction of cerebrospinal fluid flow in the ventricular system by the cells or pharmaceutical. This might lead to acute or subacute hydrocephalus. With a ventriculoperitoneal shunt implanted, it can act as a safety valve for any elevated intracranial pressure and still have the advantages of being able to be tapped multiple times. In some implementations, complications can be minimized with administration of prophylactic dexamethasone.

Figure 10:
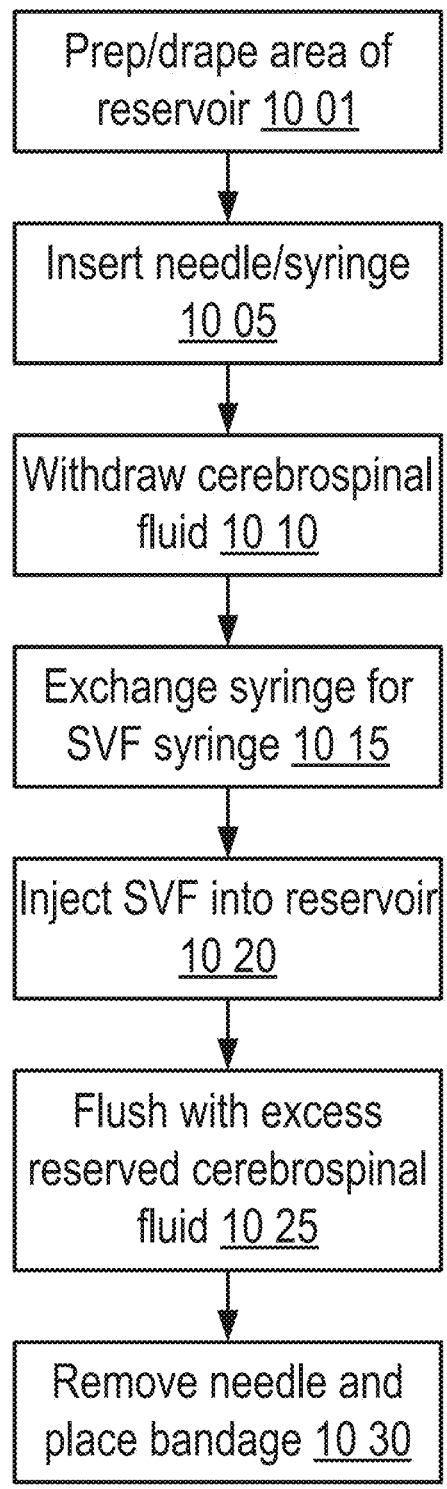
FIG. 10 shows an example of logic flow for injection of therapeutic suspensions via an Ommaya reservoir in one embodiment of a VSCS.
Figure 11:
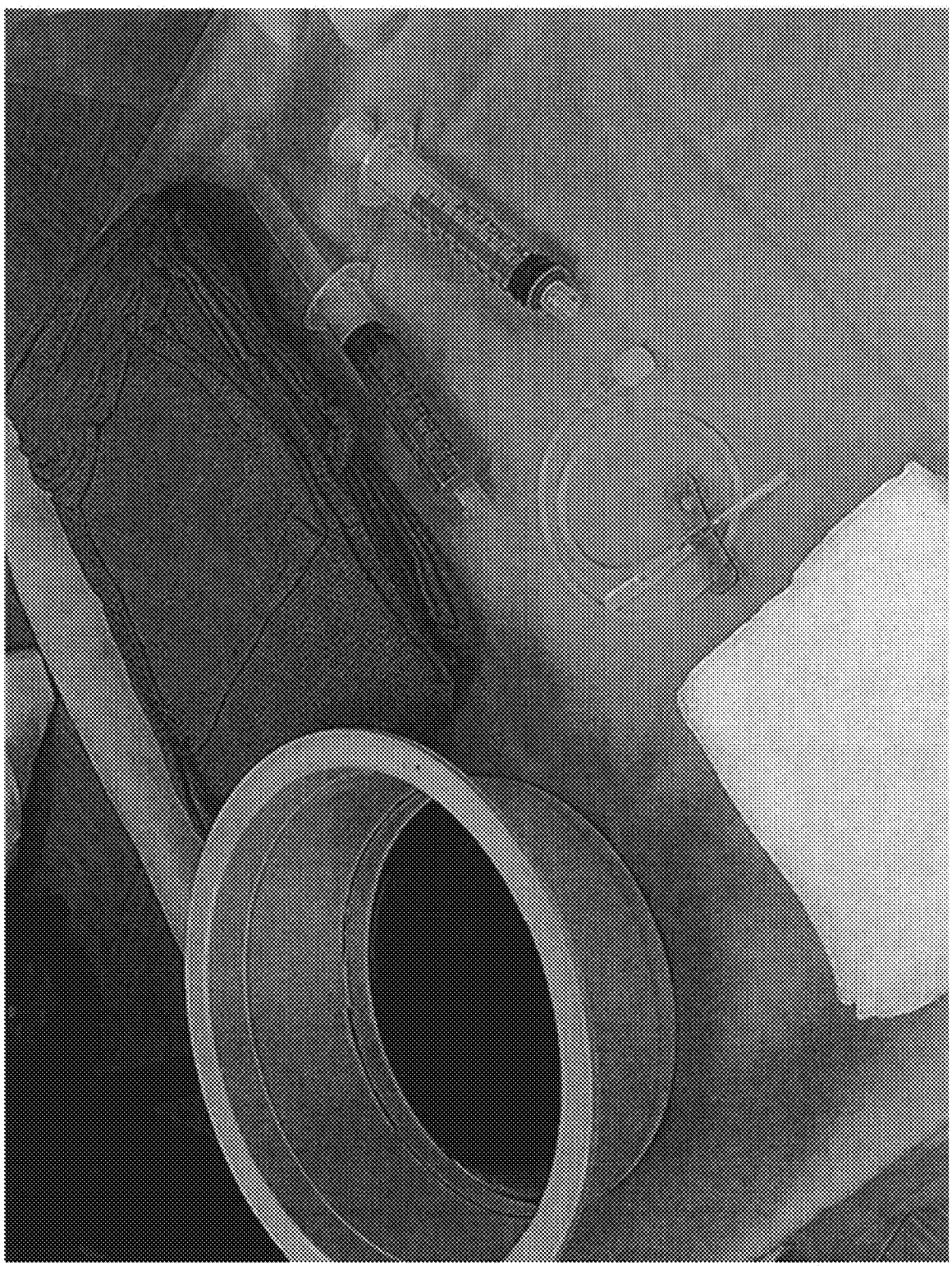
FIG. 11 shows an example of setup prior to injection of Stromal Vascular s Fraction, which is the solution in the 10 cc syringe, into the reservoir, in one embodiment.
Figure 12:
FIG. 12 shows an example of injection technique using a 21 or 23-G butterfly needle, via reservoir puncture, in one embodiment of a VSCS.

Once the Ommaya reservoir or ventriculoperitoneal shunts have been implanted into the brain, stem cells or a pharmaceutical may be injected into the Ommaya reservoir or ventriculoperitoneal shunts where they can then be instilled into the human ventricular system at any time. One advantage of these systems is the ability to use them indefinitely over time. In one embodiment, the Stromal Vascular Fraction, or purified, or expanded, autologous or allogenic stem cells, containing adipose derived stem cells or a pharmaceutical can be injected into the Ommaya reservoir or shunt using the following technique. FIG. 10 shows an example of logic flow for injection of therapeutic suspensions via an Ommaya reservoir in one embodiment of a VSCS. For example, the area of the subgaleal Ommaya reservoir may be prepped and draped 1001. A 21-gauge butterfly needle attached to a 10-cc syringe may be inserted 1005, Cerebrospinal Fluid withdrawn to a volume 1010, e.g., approximately 2 cc greater than the Stromal Vascular Fraction sample. The syringe may then be exchanged for the Stromal Vascular Fraction syringe 1015 and the Stromal Vascular Fraction fully injected into the Ommaya reservoir 1020. This may then be flushed with 2-cc of the reserved Cerebrospinal Fluid 1025, such that total volume of Cerebrospinal Fluid removed substantially equals the total volume of Stromal Vascular Fraction or therapeutic suspension injected. The needle can then be removed and sterile bandage placed over the injection site 1030. In alternative implementations, a different amount of Cerebrospinal Fluid may be withdrawn in relation to the volume of Stromal Vascular Fraction. FIG. 11 shows an example of setup prior to injection of Stromal Vascular Fraction, which is the solution in the 10 cc syringe, into the reservoir, in one embodiment. FIG. 12 shows an example of injection technique using a 21 or 23-G butterfly needle, via reservoir puncture, in one embodiment of a VSCS.

Figure 13:
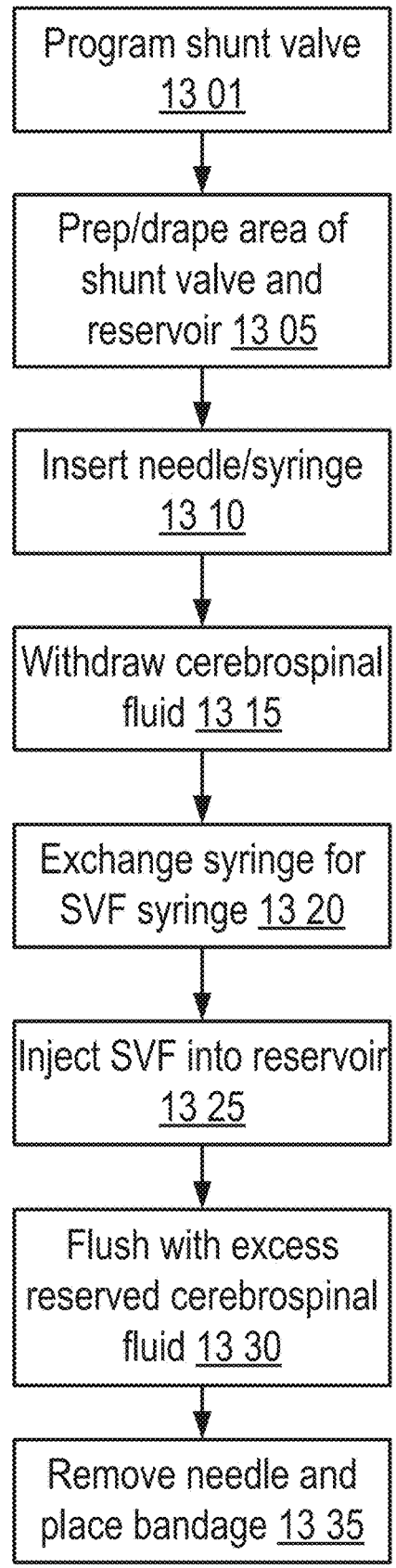
FIG. 13 shows an example of logic flow for injection of therapeutic suspensions via a ventriculoperitoneal shunt in one embodiment of a VSCS.

In another embodiment, the Stromal Vascular Fraction, or purified stem cells, containing adipose derived stem cells or a pharmaceutical can be injected into the ventriculoperitoneal shunt using the following technique. FIG. 13 shows an example of logic flow for injection of therapeutic suspensions via a ventriculoperitoneal shunt in one embodiment of a VSCS. For example, in one implementation, a programmable shunt valve may be programmed 1301, e.g., to its highest resistance (slowest flow), and the area of the subgaleal ventriculoperitoneal shunt valve and its reservoir may be prepped and draped 1305. A 21- or any gauge butterfly needle attached to a 10-cc syringe or any syringe may be inserted 1310, and Cerebrospinal Fluid may be withdrawn to a volume 1315, e.g., 2 cc greater than the Stromal Vascular Fraction sample. The syringe may then be exchanged for the Stromal Vascular Fraction syringe 1320 and the Stromal Vascular Fraction fully injected into the ventriculoperitoneal reservoir 1325. This may then be flushed with 2-cc of the reserved Cerebrospinal Fluid 1330, such that total volume of Cerebrospinal Fluid removed substantially equals the total volume of Stromal Vascular Fraction or therapeutic suspension injected. The needle can then be removed and sterile bandage placed over the injection site 1335. In alternative implementations, a different amount of Cerebrospinal Fluid may be withdrawn in relation to the volume of Stromal Vascular Fraction.

Figure 14:
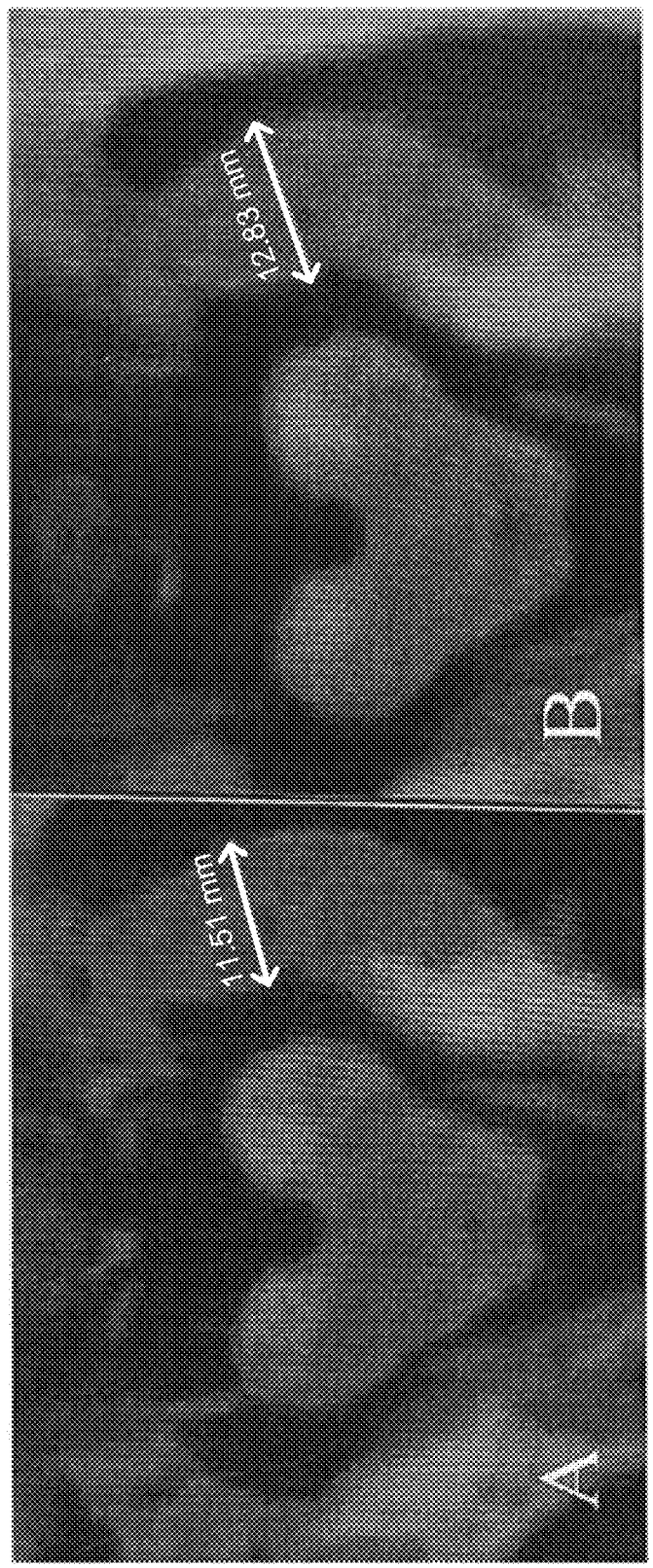
FIG. 14 shows (A) hippocampal volume less than 5th percentile for age pre-Stromal Vascular Fraction injection in an 80-year-old patient with long-standing Alzheimer's disease, and (B) 2-year post-Stromal Vascular Fraction injection, 49th percentile for age. There is a suggested correlation between patient improvement and number of injections.
Figure 15:
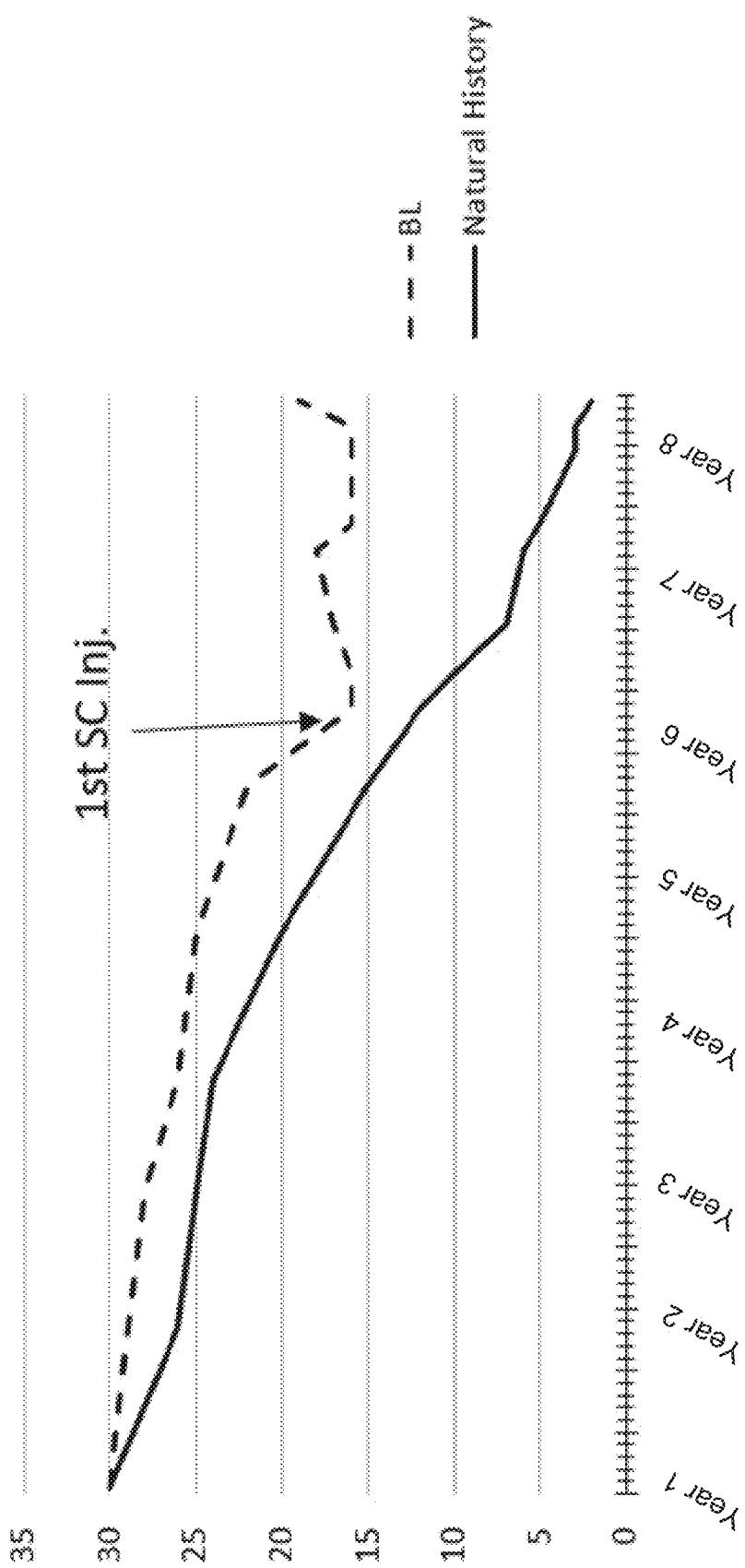
FIG. 15 shows the Mini Mental State Examination (MMSE) for an Alzheimer's Disease patient treated with certain embodiments of the VSCS compared to average Alzheimer's Disease patients versus time.
Figure 16:
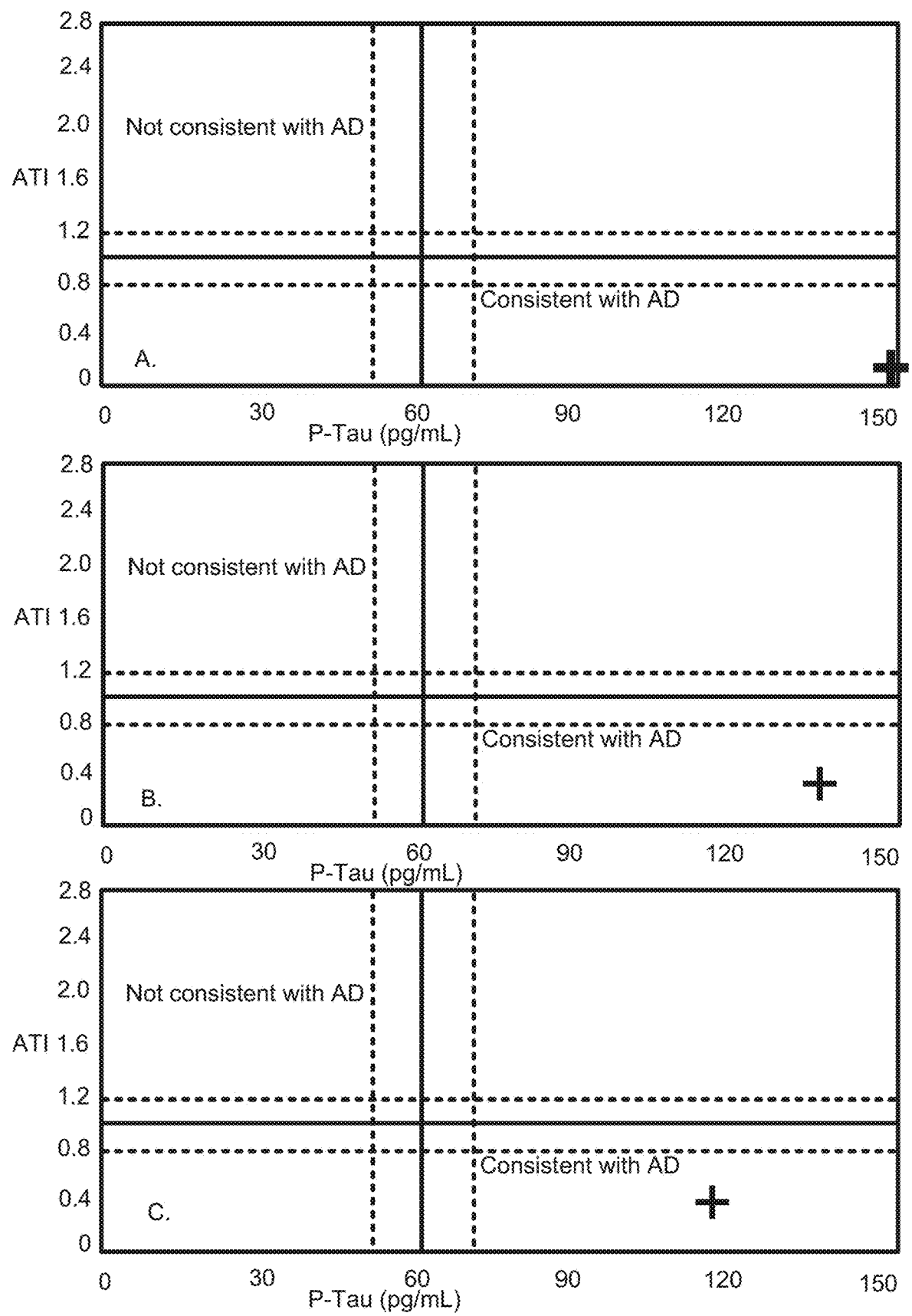
FIG. 16 shows Cerebrospinal Fluid analysis showing progressive reduction in P-Tau levels for: A. Pre-Stromal Vascular Fraction injection; B. Four months post-first Stromal Vascular Fraction injection; C. Eight months post-first Stromal Vascular Fraction injection.

Using the methods and apparatuses of the present invention, patients can receive one or more injections of stem cells or pharmaceuticals via the implanted Ommaya reservoir, ventriculoperitoneal shunt, catheter, tube, cannula, and/or the like. In one embodiment, patients may receive multiple injections. For example, multiple injections separated over months or years may be administered, and can prove to be most beneficial for the patient (e.g., where neuronal repair and/or anti-inflammatory action occurs in an upward stepwise manner), as opposed to a single intraventricular injection. Patients receiving a single injection may notice an improvement in their clinical function within the first week of injection followed by a "wearing-off" effect after 6-8 weeks. By contrast, patients who have had more than 6 injections may experience a decrease in the "wearing-off" effect to the extent that future injections could be delayed, e.g., up to 4 months. This suggests a permanence to an anti-inflammatory effect, a rebuilding of neurons and their function, and/or an epigenetic phenomenon of genetic remodeling. Other favorable outcomes of multiple injections include signs of hippocampal volume increase, stabilization and/or improvement of Memory Performance Index and/or Mild Cognitive Impairment screen, phosphorylated tau protein ("P-tau") and Traumatic Brain Injury trending toward normalization over months. For example, FIG. 14 shows (A) hippocampal volume less than 5th percentile for age pre-Stromal Vascular Fraction injection in an 80-year-old patient with long-standing Alzheimer's disease, and (B) 2-year post-Stromal Vascular Fraction injection, 49th percentile for age. There is a suggested correlation between patient improvement and number of injections. FIG. 15 shows the Mini Mental State Examination (MMSE) for an Alzheimer's Disease patient treated with certain embodiments of the VSCS compared to average Alzheimer's Disease patients versus time. FIG. 16 shows Cerebrospinal Fluid analysis showing progressive reduction in P-Tau levels for: A. Pre-Stromal Vascular Fraction injection; B. Four months post-first Stromal Vascular Fraction injection; C. Eight months post-first Stromal Vascular Fraction injection.

Embodiments of the invention may be applied in a number of neurodegenerative disorders where an inflammatory component might be implicated, such as Alzheimer's Disease and Multiple Sclerosis. Amyotrophic Lateral Sclerosis and Parkinson's Disease syndromes may also be autoimmune and inflammatory in nature, as may Traumatic Brain Injury or Chronic Traumatic Encephalopathy. Therapeutic mechanisms may include the following: 1) the promotion of angiogenesis, 2) the induction of neuronal differentiation and neurogenesis, 3) reductions in reactive gliosis, 4) the inhibition of apoptosis, 5) the expression of neurotrophic factors, 6) immunomodulatory function, and 7) facilitating neuronal integration.

While the disclosure herein focuses on injection of stem cells and/or pharmaceuticals via Ommaya reservoirs or ventriculoperitoneal shunts, it should be understood based on the disclosure herein that further embodiments are within the scope of the disclosure, such as use of a catheter, tube, cannula, and/or the like to inject stem cells into the ventricles of the brain. Any embodiment of a tube, cannula or needle may be inserted into the ventricular system for single or multiple injections. Alternatively, the techniques disclosed above may be advantageously applied using other substances such as immunoglobulin G, neurotrophic factors, endorphins, and/or the like.

In order to address various issues and advance the art, the entirety of this application for METHODS, APPARATUSES AND SYSTEMS FOR INSTILLING STEM CELLS AND PHARMACEUTICALS INTO THE HUMAN VENTRICULAR SYSTEM (including the Cover Page, Title, Headings, Field, Background, Summary, Brief Description of the Drawings, Detailed Description, Claims, Abstract, Figures, Appendices, and otherwise) shows, by way of illustration, various embodiments in which the claimed innovations may be practiced. The advantages and features of the application are of a representative sample of embodiments only, and are not exhaustive and/or exclusive. They are presented only to assist in understanding and teach the claimed principles. It should be understood that they are not representative of all claimed innovations. As such, certain aspects of the disclosure have not been discussed herein. That alternate embodiments may not have been presented for a specific portion of the innovations or that further undescribed alternate embodiments may be available for a portion is not to be considered a disclaimer of those alternate embodiments. It will be appreciated that many of those undescribed embodiments incorporate the same principles of the innovations and others are equivalent. Thus, it is to be understood that other embodiments may be utilized and functional, logical, operational, organizational, structural and/or topological modifications may be made without departing from the scope and/or spirit of the disclosure. As such, all examples and/or embodiments are deemed to be non-limiting throughout this disclosure. Also, no inference should be drawn regarding those embodiments discussed herein relative to those not discussed herein other than it is as such for purposes of reducing space and repetition. For instance, it is to be understood that the logical and/or topological structure of any combination of any process steps and/or feature sets as described in the figures and/or throughout are not limited to a fixed operating order and/or arrangement, but rather, any disclosed order is exemplary and all equivalents, regardless of order, are contemplated by the disclosure. Similarly, some features are applicable to one aspect of the innovations, and inapplicable to others. In addition, the disclosure includes multiple innovations including some that may not be presently claimed, and the Applicant reserves all rights in those presently unclaimed innovations including the right to claim such innovations, file additional applications, continuations, continuations in part, divisionals, and/or the like thereof. As such, it should be understood that advantages, embodiments, examples, functional, features, logical, operational, organizational, structural, topological, and/or other aspects of the disclosure are not to be considered limitations on the disclosure as defined by the claims or limitations on equivalents to the claims.

What is claimed is:

1. A method, comprising:
   attaching a therapeutic syringe to a needle inserted into an injection site for at least one reservoir coupled to a ventricular system of a brain, wherein the therapeutic syringe contains a therapeutic suspension comprising stem cells, wherein the stem cells comprise a stromal vascular fraction of adipose derived mesenchymal stem cells;
   injecting the therapeutic suspension into the at least one reservoir; and
   removing the needle and dressing the injection site.

2. The method of claim 1, wherein the at least one reservoir is an Ommaya reservoir.

3. The method of claim 2, wherein the Ommaya reservoir is subgaleal.

4. The method of claim 1, wherein the at least one reservoir is coupled to a ventriculoperitoneal shunt.

5. The method of claim 4, wherein the ventriculoperitoneal shunt comprises a programmable shunt valve.

6. The method of claim 5, further comprising:
   programming the programmable shunt valve to a slowest flow level.

7. The method of claim 1, wherein the therapeutic suspension further comprises a pharmaceutical.

8. The method of claim 1, further comprising:
   before attaching the therapeutic syringe:
      inserting the needle attached to a first syringe into the injection site for the at least one reservoir coupled to the ventricular system of the brain before attaching the therapeutic syringe;
      withdrawing a first volume of cerebrospinal fluid using the first syringe;
      exchanging the first syringe attached to the needle with the therapeutic syringe; and
   after injecting the therapeutic suspension:
      flushing the at least one reservoir with a portion of the first volume of cerebrospinal fluid.

9. The method of claim 8, wherein the first volume of cerebrospinal fluid substantially equals a volume of the therapeutic suspension.

10. The method of claim 1, further comprising:
    performing liposuction to obtain a lipo-aspirate solution;
    condensing the lipo-aspirate solution by centrifugation to obtain a condensed lipo-aspirate solution;
    adding a collagenase solution to the condensed lipo-aspirate solution to obtain a digested lipo-aspirate solution;
    incubating the digested lipo-aspirate solution to obtain an incubated lipo-aspirate solution;
    washing the incubated lipo-aspirate solution to obtain a washed lipo-aspirate solution; and
    isolating the stromal vascular fraction from the washed lipo-aspirate solution.

11. The method of claim 10, wherein isolating the stromal vascular fraction from the washed lipo-aspirate solution further comprises:
    filtering the washed lipo-aspirate solution through a cell strainer.

12. The method of claim 10, further comprising:
performing photomicrography on the stromal vascular fraction.

13. The method of claim 10, further comprising:
expanding the stromal vascular fraction via cell isolation and expansion in a certified cell bank.

14. The method of claim 1, wherein the at least one reservoir coupled to the ventricular system of the brain is coupled by a right-angle connection of a right frontal intraventricular catheter.

15. The method of claim 1 further comprising:
implanting the at least one reservoir.

16. The method of claim 15, wherein implanting the at least one reservoir further comprises:
applying an incision to the right frontal region of the patient's head for ventricular access;
applying a burr hole at the incision;
opening and coagulating the dura at the burr hole;
inserting a ventricular catheter into the ventricular system of the brain;
connecting the ventricular catheter to the at least one reservoir, the at least one reservoir being an Ommaya reservoir; and
closing the incision.

17. The method of claim 15, wherein implanting the at least one reservoir further comprises:
applying an incision to the right frontal region of the patient's head for ventricular access;
applying a burr hole at the incision;
opening and coagulating the dura at the burr hole;
inserting a cannula into the ventricular system of the brain;
connecting the cannula to a valve and a peritoneal catheter in series; and
closing the incision.

18. The method of claim 17, wherein the valve is a programmable valve.

\* \* \* \* \*